US010226181B2

(12) United States Patent
Oishi

(10) Patent No.: US 10,226,181 B2
(45) Date of Patent: Mar. 12, 2019

(54) OBJECT INFORMATION ACQUIRING APPARATUS AND DISPLAY METHOD

(71) Applicant: CANON KABUSHIKI KAISHA, Tokyo (JP)

(72) Inventor: Takuji Oishi, Kyoto (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 14/134,778

(22) Filed: Dec. 19, 2013

(65) Prior Publication Data

US 2014/0187924 A1  Jul. 3, 2014

(30) Foreign Application Priority Data

Dec. 28, 2012  (JP) .................................. 2012-286549

(51) Int. Cl.
*A61B 5/00* (2006.01)
*A61B 5/1455* (2006.01)
(Continued)

(52) U.S. Cl.
CPC .......... *A61B 5/0095* (2013.01); *A61B 5/0093* (2013.01); *A61B 5/14551* (2013.01);
(Continued)

(58) Field of Classification Search
None
See application file for complete search history.

(56) References Cited

U.S. PATENT DOCUMENTS

2004/0127777 A1* 7/2004 Ruchti ................. A61B 5/0071
  600/316
2007/0238958 A1* 10/2007 Oraevsky ............. A61B 5/0073
  600/407
(Continued)

FOREIGN PATENT DOCUMENTS

JP   2006-110028    4/2006
JP   2011-526514    10/2011

OTHER PUBLICATIONS

Liu, Bo, et al. "Assessment of photoacoustic computed tomography to classify tissue in a polycystic-kidney disease mouse model." Biomedical Optics 2006. International Society for Optics and Photonics, 2006.*

(Continued)

*Primary Examiner* — Carolyn Pehlke
(74) *Attorney, Agent, or Firm* — Venable LLP

(57) ABSTRACT

An object information acquiring apparatus comprises a light irradiation unit configured to irradiate lights having different wavelengths respectively; an acoustic wave receiving unit configured to receive an acoustic wave by each of the lights having different wavelengths respectively, and convert into an electric signal that corresponds to each of the lights having different wavelengths; a characteristic information acquiring unit configured to acquire characteristic distribution related to each position in the object based on the electric signal; a statistics acquiring unit configured to acquire a histogram from the characteristic distribution; and an image information acquiring unit configured to acquire image information causing a display device to display the characteristic distribution in the object and the histogram.

15 Claims, 9 Drawing Sheets

(51) Int. Cl.
*G01N 21/17* (2006.01)
*G06T 7/00* (2017.01)

(52) U.S. Cl.
CPC ...... *A61B 5/14552* (2013.01); *G01N 21/1702* (2013.01); *G06T 7/0012* (2013.01)

(56) References Cited

U.S. PATENT DOCUMENTS

| | | | |
|---|---|---|---|
| 2009/0324033 A1 | 12/2009 | Addison et al. | 382/128 |
| 2010/0256493 A1* | 10/2010 | Chono | A61B 8/08 600/443 |
| 2013/0160558 A1 | 6/2013 | Oishi | 73/655 |
| 2013/0261427 A1 | 10/2013 | Oishi | 600/407 |
| 2013/0336551 A1* | 12/2013 | Clingman | A61B 5/0095 382/128 |
| 2014/0007878 A1* | 1/2014 | Armitstead | A61B 5/083 128/204.23 |
| 2014/0018645 A1 | 1/2014 | Wada et al. | 600/316 |

OTHER PUBLICATIONS

Reschenhofer, Erhard. "The bimodality principle." J Stat Educ 9.1 (2001): 1-16.*

Zeng, Lvming, et al. "3D-visual laser-diode-based photoacoustic imaging." Optics express 20.2 (2012): 1237-1246.*

NIST/SEMATECH e-Handbook of Statistical Methods (http://www.itl.nist.gov/div898/handbook/, Jun. 1, 2003).*

Baecker (Workshop: Image processing and analysis with ImageJ and MRI Cell Image Analyzer, Apr. 30, 2010).*

Cox, B. T., J. G. Laufer, and P. C. Beard. "The challenges for quantitative photoacoustic imaging." In Proc. SPIE, vol. 7177, p. 717713. 2009.*

X. Wang et al., "Noninvasive imaging of hemoglobin concentration and oxygenation in the rat brain using high-resolution photoacoustic tomography", *Journal of Biomedical Optics*, 11 (2) (Mar./Apr. 2006).

JPO Office Action dated Nov. 2016 in counterpart Japanese patent application 2012-286549, with translation.

* cited by examiner

OBJECT INFORMATION ACQUIRING APPARATUS AND DISPLAY METHOD

BACKGROUND OF THE INVENTION

Field of the Invention

The present invention relates to a technique of displaying image data in an object information acquiring apparatus.

Description of the Related Art

Many proposals have been made for techniques to capture a tomographic image inside an object in a noninvasive way. One such technique is photoacoustic tomography (PAT) that acquires bio-function information using light and ultrasound.

Photoacoustic tomography is a technique that irradiates an object with pulsed light generated in a light source, receives and analyzes photoacoustic waves (typically ultrasonic waves) generated by the light that is absorbed in the object, and generates an image of the internal tissue. By detecting time-based changes of the received acoustic waves at a plurality of locations and mathematically analyzing and reconstructing the acquired signals, information related to optical characteristics, such as the absorption coefficient inside an object, can be visualized.

Near-infrared light can easily transmit through water which constitutes most of an organism, and is easily absorbed by hemoglobin in blood, therefore a vascular image can be acquired if near-infrared light is used for pulsed light. Furthermore, oxygen saturation in blood, which is function information, can be measured by comparing vascular images acquired by pulsed lights having different wavelengths. Since the oxygen saturation of blood around a malignant tumor should be lower than that of blood around a benign tumor, it is expected that knowing the oxygen saturation assists in distinguishing a benign from a malignant tumor.

A known technique related to this art is disclosed, for example, in the following document: "Noninvasive imaging of hemoglobin concentration and oxygenation in the rat brain using high-resolution photoacoustic tomography" by Xueding Wang et al, Journal of Biomedical Optics 11(2), 024015, March/April 2006)

"Noninvasive imaging of hemoglobin concentration and oxygenation in the rat brain using high-resolution photoacoustic tomography" document discloses a photoacoustic tomography apparatus that distinguishes a signal portion which is a portion where blood is assumed to exist and a background portion which is a portion other than the signal portion, based on a measured absorption coefficient inside the object, and creates and displays only the oxygen saturation distribution of the signal portion.

SUMMARY OF THE INVENTION

If the primary light absorbers in an object are oxyhemoglobin and deoxyhemoglobin, the oxygen saturation is calculated as follows.

The absorption coefficient $\mu_a(\lambda)$ acquired by measurement using the light with wavelength $\lambda$ is a sum of a product of an absorption coefficient $\varepsilon_{ox}(\lambda)$ of the oxyhemoglobin and an abundance ratio $C_{ox}$ of oxyhemoglobin, and a product of an absorption coefficient $\varepsilon_{de}(\lambda)$ of a deoxyhemoglobin and an abundance ratio $C_{de}$ of the deoxyhemoglobin. In other words, $\mu_a(\lambda)$ is given by Expression 1.

[Math. 1]

$$\mu_a(\lambda) = \varepsilon_{ox}(\lambda) \cdot C_{ox} + \varepsilon_{de}(\lambda) \cdot C_{de} \quad \text{(Expression 1)}$$

$\varepsilon_{ox}(\lambda)$ and $\varepsilon_{de}(\lambda)$ are physical properties of which values are predetermined, and have been measured in advance by a certain method. Since there are two unknown quantities in Expression 1, $C_{ox}$ and $C_{de}$, $C_{ox}$ and $C_{de}$ can be calculated by simultaneous equations by performing measurement at least twice using light having a different wavelength. If the measurement is performed using light with many wavelengths, $C_{ox}$ and $C_{de}$ can be acquired by fitting based on the least squares method.

The oxygen saturation $SO_2$, which is a ratio of the oxyhemoglobin in all hemoglobin, can be calculated by Expression 2.

[Math. 2]

$$SO_2 = \frac{C_{ox}}{C_{de} + C_{ox}} \quad \text{(Expression 2)}$$

If the measurement is performed using two types of wavelengths, $\lambda_1$ and $\lambda_2$, the oxygen saturation $SO_2$ is expressed as Expression 3 by substituting $C_{ox}$ and $C_{de}$ acquired by solving the simultaneous equations of Expression 1 for those in Expression 2, and Expression 3 can be transformed into Expression 4.

[Math. 3]

$$SO_2 = \frac{-\mu_a(\lambda_1)\varepsilon_{de}(\lambda_2) + \mu_a(\lambda_2)\varepsilon_{de}(\lambda_1)}{-\mu_a(\lambda_1)\{\varepsilon_{de}(\lambda_2) - \varepsilon_{ox}(\lambda_2)\} + \mu_a(\lambda_2)\{\varepsilon_{de}(\lambda_1) - \varepsilon_{ox}(\lambda_1)\}} \quad \text{(Expression 3)}$$

[Math. 4]

$$SO_2 = \frac{-\frac{\mu_a(\lambda_1)}{\mu_a(\lambda_2)}\varepsilon_{de}(\lambda_2) + \varepsilon_{de}(\lambda_1)}{-\frac{\mu_a(\lambda_1)}{\mu_a(\lambda_2)}\{\varepsilon_{de}(\lambda_2) - \varepsilon_{ox}(\lambda_2)\} + \{\varepsilon_{de}(\lambda_1) - \varepsilon_{ox}(\lambda_1)\}} \quad \text{(Expression 4)}$$

Oxygen saturation distribution here refers to the values of oxygen saturations in an object expressed two-dimensionally or three-dimensionally, which is an image expressing the values of oxygen saturations by color or brightness.

In photoacoustic tomography, as the depth of a segment of an object to be measured becomes deeper, the quantity of light that reaches that segment decreases, and the generated acoustic waves become weak. In other words, as the measurement target segment becomes deeper, the signal-to-noise (SN) ratio of the absorption coefficient to be measured deteriorates, and measurement errors increase. If the denominator term of the SN ratio of the absorption coefficient changes when the SN ratio of the absorption coefficient is poor, the calculated oxygen saturation changes considerably. In other words, errors in oxygen saturation distribution increase, and it becomes difficult to distinguish the portion to be observed, that is the portion where blood exists.

In the photoacoustic tomography apparatus according to the above mentioned document, oxygen saturation distribution is generated and displayed with distinguishing the signal portion and the background portion using a measured absorption coefficient. However as the measurement target location in the object becomes deeper, errors in an absorption coefficient increase, which means that accurately distinguishing the signal portion and the background portion becomes more difficult as the measurement target location becomes deeper. Therefore the technique disclosed in the above mentioned document cannot solve the problem of accurately discerning an area where blood exists.

Further, the oxygen saturation distribution of an area where the SN ratio is poor, such as the deep part of an object, does not have even values but has dispersed values, which makes it difficult to read the properties (characteristics of the distribution, including approximate values, errors and continuity) by visually observing the oxygen saturation distribution. In particular, if the oxygen saturation distribution is three-dimensional, the distribution in the three-dimensional space is displayed on the display as a two-dimensional image, therefore it is difficult to grasp the distribution at a glance, and reading the oxygen saturation values becomes even more difficult.

To solve this problem, it is necessary to accurately read the properties of the oxygen saturation distribution of the target area even if an area where the SN ratio is poor is measured.

With the foregoing in view, it is an object of the present invention to provide an object information acquiring apparatus that can accurately evaluate the oxygen saturation distribution.

The present invention in its one aspect provides an object information acquiring apparatus comprising a light irradiation unit configured to irradiate an object with lights having different wavelengths respectively; an acoustic wave receiving unit configured to receive an acoustic wave that is generated from the object by each of the lights having different wavelengths respectively, and convert the received acoustic wave into an electric signal that corresponds to each of the lights having different wavelengths; a characteristic information acquiring unit configured to acquire characteristic distribution indicating characteristic information related to each position in the object based on the electric signal; a statistics acquiring unit configured to acquire a histogram from the characteristic distribution in the object; and an image information acquiring unit configured to acquire image information causing a display device to display the characteristic distribution in the object and the histogram.

The present invention in its another aspect provides a display method, comprising a statistics acquiring step of acquiring characteristic distribution in an object based on a receive signal of an acoustic wave that is generated from the object by each of lights having different wavelengths respectively, and acquiring a histogram from the characteristic distribution; an image information acquiring step of acquiring image information for displaying the characteristic distribution in the object and the histogram on a display device; and an image display step of displaying the image information.

According to the present invention, an object information acquiring apparatus that can accurately evaluate the oxygen saturation distribution can be provided.

Further features of the present invention will become apparent from the following description of exemplary embodiments with reference to the attached drawings.

DESCRIPTION OF THE EMBODIMENTS

Embodiments of the present invention will now be described with reference to the drawings. As a rule, identical composing elements are denoted with a same reference number, for which redundant description is omitted.

Embodiment 1

A photoacoustic diagnostic apparatus according to Embodiment 1 of the present invention is an apparatus configured to irradiate an object with measurement light and analyze a photoacoustic wave generated by the measurement light, whereby distribution of oxygen saturations inside an organism (the object) is imaged. In concrete terms, this apparatus displays an image of the oxygen saturation distribution, and displays statistics in a region of interest that is set, as shown in FIG. 2A to FIG. 2D. First the composing elements, then the processing method and finally the effect thereof will be described.

The oxygen saturation, the absorption coefficient or the like are the object information that represent characteristic information inside the object. In other words, the photoacoustic diagnostic apparatus according to this embodiment is also called an "object information acquiring apparatus".

<System Configuration>

Figure 1:
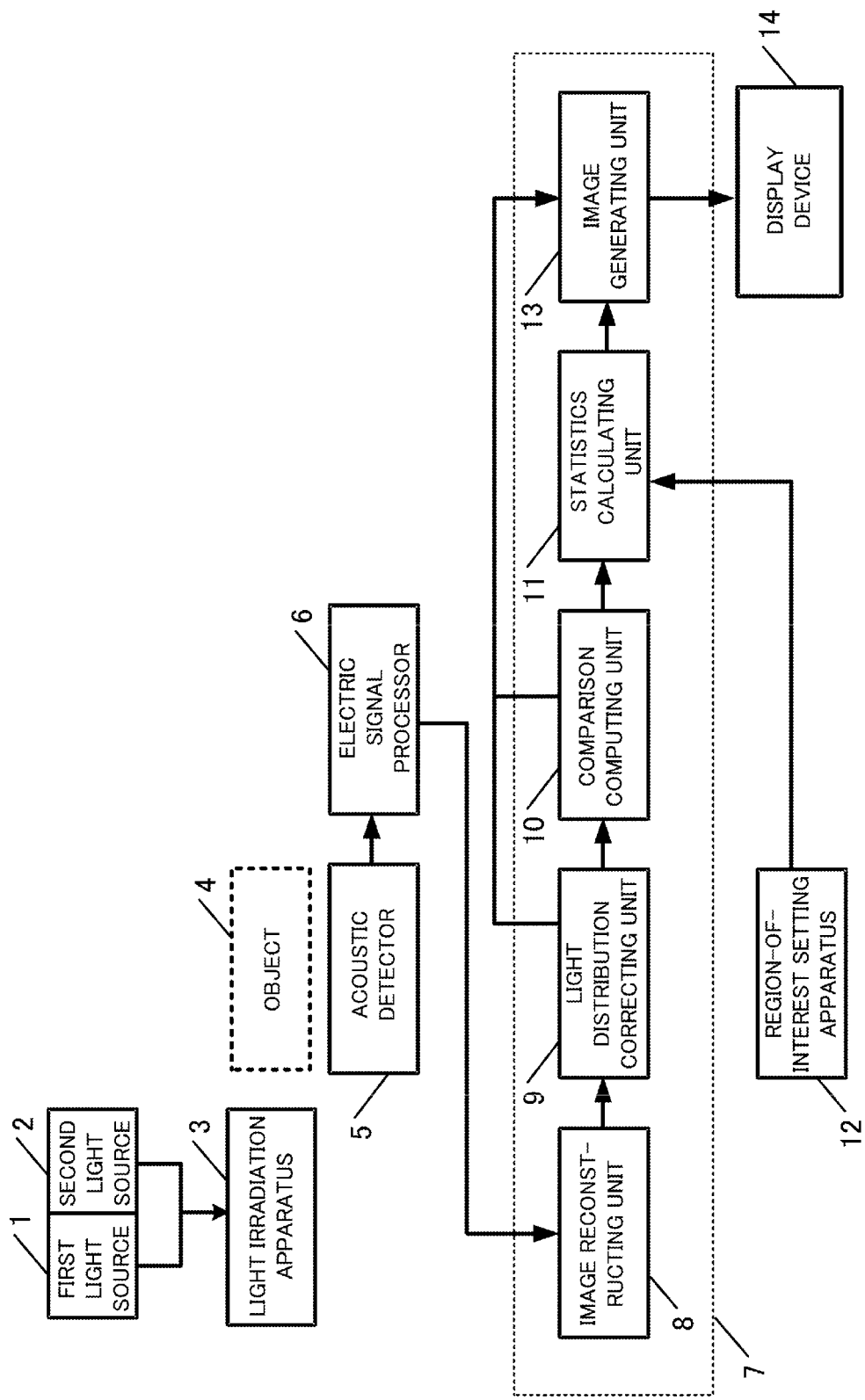
FIG. 1 is a diagram depicting a system configuration of a photoacoustic diagnostic apparatus according to Embodiment 1.

First a configuration of the photoacoustic diagnostic apparatus according to Embodiment 1 will be described with reference to FIG. 1. The photoacoustic diagnostic apparatus according to Embodiment 1 is constituted by a first light source 1, a second light source 2, a light irradiation apparatus 3, an object 4, an acoustic detector 5, an electric signal processor 6, a data processor 7, a region-of-interest setting apparatus 12, and a display device 14. The data processor 7 includes an image reconstructing unit 8, a light distribution correcting unit 9, a comparison computing unit 10, a statistics calculating unit 11, and an image generating unit 13.

<<Light Sources 1 and 2>>

The first light source 1 and the second light source 2 are apparatuses that generate pulsed light. Each light source is preferably a laser light source to acquire large output, but may be a light emitting diode or the like. In order to effectively generate a photoacoustic wave, light must be irradiated in a sufficiently short time according to the thermal characteristics of the object. If the object is a living body, it is preferable that the pulse width of the pulsed light generated from the light source does not exceed several tens of nanoseconds. The wavelength of the pulsed light is preferably about 700 nm to 1200 nm. Light in this range can reach a relatively deep part of an organism and acquire information, therefore [this wavelength range] is called the "near infrared window". The wavelength of the pulsed light preferably has a high absorption coefficient with respect to the observation object.

The wavelength of the pulsed light emitted from the first light source 1 and the wavelength of the pulsed light emitted from the second light source 2 are different from each other.

The wavelengths of these light sources are preferably completely different in terms of the absorption coefficient of the oxyhemoglobin and the absorption coefficient of the deoxyhemoglobin respectively. Then error propagation in the oxygen saturation can be decreased, and the measurement accuracy of the oxygen saturation can be improved.

It is preferable that the timing to emit the pulsed light from the first light source 1 and the timing to emit the pulsed light from the second light source 2 are different. This is because the absorption coefficient must be measured individually using a respective wavelength.

Two light sources are used in this embodiment, but a single light source which functions as both the first light source and the second light source may be used if the light source is a wavelength variable laser.

<<Light Irradiation Apparatus 3>>

The light irradiation apparatus 3 is an apparatus that guides a pulsed light generated in the first light source 1 or the second light source 2 to the object 4. In concrete terms, [the light irradiation apparatus 3] is constituted by such optical devices as an optical fiber, a lens, a mirror and a diffusion plate. Using these optical devices, the irradiation conditions, such as the irradiation shape of the pulse light, the optical density and the irradiation direction to the object can be freely set. The optical devices that constitute the light irradiation apparatus 3 is not limited to these devices, but may be any device that can satisfy the above mentioned functions.

The first light source 1, the second light source 2 and the light irradiation apparatus 3 constitute the light irradiation unit according to the present invention.

<<Object 4>>

The object 4 is not a constituent of the present invention, but it is described here nonetheless.

The object 4 is a measurement object. The object 4 is typically an organism, but may be a phantom simulating acoustic characteristic and an optical characteristic of an organism. The photoacoustic diagnostic apparatus can image a light absorber having a large light absorption coefficient which exists inside the object 4. If the object is an organism, the imaging target is hemoglobin, water, melanin, collagen, lipids or the like. If the object is a phantom, a substance simulating optical characteristic of any one of the above mentioned substances is enclosed inside the phantom, instead of the light absorber. Further, a contrast medium, a molecular probe or the like may be injected into the organism or the phantom as the object.

<<Acoustic Detector 5>>

The acoustic detector 5 is a unit that converts an acoustic wave generated inside the object 4 into an analog electric signal. The acoustic detector 5 may be a single acoustic detector or may be constituted by a plurality of acoustic detectors. The acoustic detector 5 must be installed to acoustically couple with the object 4, in order to eliminate the influence of reflection and attenuation of the acoustic wave. For example, it is preferable that an acoustic matching material, such as acoustic matching gel, water and oil, is disposed between the acoustic detector 5 and the object 4.

It is preferable that the acoustic detector 5 has high sensitivity and a wide frequency band. In concrete terms, [the acoustic detector 5] is constituted by piezoelectric ceramics (PZT), polyvinylidene fluoride resin (PVDF), capacitive micro-machined ultrasonic transducer (CMUT) or a Fabry-Perot interferometer is used. [The acoustic detector 5] is not limited to these examples, but can be any component if the functions are satisfied.

In order to acquire data in a wide range, the light irradiation apparatus 3 and the acoustic detector 5 may be configured to be movable, so that the object can be continuously measured while sequentially changing the pulse light irradiation position on the surface of the object.

<<Electric Signal Processor 6>>

The electric signal processor 6 is a unit that amplifies an analog electric signal acquired by the acoustic detector 5, and converts [the amplified analog electric signal] into a digital signal. The electric signal processor 6 is, for example, an amplifier constituted by electric circuits or an analog-digital converter (ADC). In order to efficiently acquire data, a same number of amplifiers or ADCs as the number of receive elements of the acoustic detector 5 are disposed, but one amplifier or ADC may be connected [with each receive element] in sequence.

The acoustic detector 5 and the electric signal processor 6 constitute the acoustic wave receiving unit according to the present invention.

<<Data Processor 7>>

The data processor 7 is a unit that processes digitized signals or numeric data, and generates an image to be displayed on the display device 14. The data processor 7 includes the image reconstructing unit 8, the light distribution correcting unit 9, the comparison computing unit 10, the statistics calculating unit 11 and the image generating unit 13.

The data processor 7 is a computer constituted by a CPU, a DRAM, a non-volatile memory and a control port (not illustrated). Each module is controlled by the CPU, which executes programs stored in the non-volatile memory. In this embodiment, the data processor 7 is a computer, but may be specially designed hardware.

The image reconstructing unit 8 is a unit that reconstructs digitized signals, and generates an image that indicates the distribution of the initial sound pressure in the sound source. The image that indicates the initial sound pressure distribution is generated for each wavelength of the light source. For the reconstruction processing method, a universal back projection method, which propagates and superimposes the differentiated signal in reverse from the position where the signal was acquired, is preferable, but can be any method if an image can be constructed from signals.

The light distribution correcting unit 9 is a unit that generates an absorption coefficient distribution of an absorber by calculating the attenuation of light that entered the object, and dividing the initial sound pressure distribution by light distribution. The initial sound pressure p of the photoacoustic wave depends on the light intensity $\phi$ as the relationship in Expression 5 shows. Here $\Gamma$ denotes a Gruneisen constant, and $\mu_a$ denotes an absorption coefficient.

[Math. 5]

$$p = \Gamma \cdot \phi \cdot \mu_a \quad \text{(Expression 5)}$$

When light enters the object, the light is scattered and absorbed in the object, and the light intensity drops exponentially with respect to the propagation distance. Therefore the distribution of the light intensity $\phi$ in the object can be estimated by the intensity distribution of the light irradiated onto the object and by the shape of the object. In the case of an organism, the Gruneisen constant can be regarded as a fixed value. This means that the absorption coefficient distribution is given by dividing the initial sound pressure distribution by the light intensity distribution and the Gruneisen constant Γ. If only the relative value of the absorption coefficient distribution is required, division by the Gruneisen constant is unnecessary.

The light intensity distribution in the object is different depending on the wavelength of the light, hence the absorption coefficient distribution is calculated for each wavelength. In this embodiment, the absorption coefficient distribution corresponding to the wavelength of the first light source is called the "first absorption coefficient distribution", and the absorption coefficient distribution corresponding to the wavelength of the second light source is called the "second absorption coefficient distribution".

The comparison computing unit 10 is a unit that generates the oxygen saturation distribution by comparing the first absorption coefficient distribution and the second absorption coefficient distribution. The computation of the oxygen saturation must be started after all the absorption coefficient distribution data corresponding to a plurality of wavelengths are completed, therefore while acquiring absorption coefficient distribution data corresponding to other wavelengths, the comparison computing unit 10 temporarily stores the absorption coefficient distribution data acquired thus far.

As mentioned above, the oxygen saturation distribution can be acquired by substituting the acquired absorption coefficient distribution data in Expression 3. If three or more light sources are used, the oxygen saturation distribution can be acquired by determining $C_{ox}$ and $C_{de}$ by the least squares method, and substituting $C_{ox}$ and $C_{de}$ in Expression 2.

The image reconstructing unit 8, the light distribution correcting unit 9 and the comparison computing unit 10 are the characteristic information acquiring unit according to the present invention, and the generated oxygen saturation distribution is the characteristic distribution according to the present invention.

The statistics calculating unit 11 is a unit that calculates the statistics of the oxygen saturation distribution in a region of interest, which is set by the region-of-interest setting apparatus 12, which will be described later. Statistics are information expressing the characteristics of the oxygen saturation. The statistics calculated by the statistics calculating unit 11 may be a single type or a plurality of types. Details on the statistics and a calculation method thereof will be described later.

It is preferable to use an oxygen saturation value of each pixel to calculate the statistics, but a representative value of a set of pixels in a certain range, or a value of an interpolated point acquired by interpolating pixels may be used for the calculation. In this embodiment, the statistics are calculated using a value of each pixel.

The statistics calculating unit 11 is the statistics acquiring unit according to the present invention.

The image generating unit 13 is a unit that generates an image to be presented to the operator. FIG. 2A to FIG. 2D show examples of images generated by the image generating unit 13. An image generated by the image generating unit 13 includes an oxygen saturation distribution, a region of interest and calculated statistics. By including this information in a same image, the operator can easily know the characteristics of the oxygen saturation. [The operator] can also interactively check the change of the statistics with respect to the region of interest. In other words, diagnosis becomes easier.

The image to be generated is an image displayed by one display device, and all [information] need not be included in one image. For example, a first image to display the oxygen saturation distribution in the main window and a second image to display the statistics in the sub-window may be generated.

The image generating unit 13 is the image acquiring unit according to the present invention, and an image generated by the image generating unit 13 is the image information according to the present invention.

<<Region-of-Interest Setting Apparatus 12>>

The region-of-interest setting apparatus 12 is a unit that sets a range of calculating the statistics in the oxygen saturation distribution generated by the comparison computing unit 10. The region-of-interest setting apparatus 12 is, for example, an input interface, such as a keyboard, a mouse, a touch pen and a touch panel, or a computer that includes a display.

It is preferable to manually set a region of interest, which is a region the operator is focusing on, but if the region of interest is the same as a previous measurement, or if it can be set based on a predetermined rule, the region of interest may be automatically set by storing the predetermined location or the predetermined rule in advance. The region of interest may be generally set manually and finely set automatically, or vice verse. Manual setting and automatic setting can be combined.

The region-of-interest setting apparatus 12 is the region of interest setting unit according to the present invention.

In the case of manually setting the region of interest, the oxygen saturation distribution is displayed on the display device 14, and the operator sets [the region of interest] using the input interface, such as a mouse, while looking at the image. For the setting, it is preferable to draw a closed curve, which is a boundary of the region of interest, on the image by freehand. Thereby the operator can set the region of interest as desired. [The region of interest] may also be set by placing a predetermined close curve, such as a geometric shape, and changing the scale, angle, aspect ratio, position or the like. This makes it easy to set the region of interest. The coordinates of the closed curve may be set by numeric values or by functions using a keyboard, for example. If the range of the region of interest is set by numeric values, the setting can be easily reproduced.

If the oxygen saturation distribution is three-dimensional data, a three-dimensional region of interest may be set. If the oxygen saturation distribution is three-dimensional, the oxygen saturation is displayed on the display device 14 by volume rendering, or in a three cross-sectional display. The region of interest may also be set by inputting the desired coordinates while rotating the displayed three-dimensional object. This allows setting the region of interest while checking the position in space. The region of interest may also be set by positioning a predetermined three-dimensional shape in the space and changing the scale, angle, aspect ratio, position or the like.

The region of interest may be set using a dedicated interface that can read coordinates in a three-dimensional space. If the oxygen saturation distribution is displayed by a three cross-sectional display, the region of interest of the three-dimensional object may be set by setting the region of interest for each cross-section. This allows directly drawing the region of interest in each cross-section, which makes interactive setting possible.

A plurality of region of interests may be set. For example, a first region of interest that includes the entire region of the oxygen saturation distribution and a second region of interest that includes only the target area may be set. In this case, the first region of interest may be automatically set and the second region of interest may be manually set. If a plurality of regions of interest are set like this, the statistics of these regions can be compared, and the characteristics of the oxygen saturation distribution of these areas can be compared.

<<Display Device 14>>

The display device 14 is a unit that displays an image generated by the image generating unit 13, and is typically a standard display device. The display device 14 can also be used as an output interface when a region of interest is specified. The display device 14 is not an essential composing element of the present invention.

Statistics Calculation Examples

Now examples of statistics that are outputted by the statistics calculating unit 11 and a method of calculating statistics individually will be described.

It is preferable that the statistics outputted by the statistics calculating unit 11 is a histogram where a number of pixels in a region of interest is indicated for each oxygen saturation. Thereby the characteristics of the oxygen saturation in the region of interest can be read intuitively.

The statistics outputted by the statistics calculating unit 11 may be values indicating uni-modality/multi-modality in the histogram.

For example, these values can be calculated by differentiating the histogram, and counting a number of locations where the plus and minus of a differentiated value are inverted. The histogram becomes multi-modal if a plurality of types of absorbers having different oxygen saturations exist in the region of interest, and the histogram becomes uni-modal if only one type of absorber exists in the region of interest.

Therefore whether a plurality of types of absorbers or a single type of absorber exist(s) in the region of interest can be determined by calculating the values that indicate uni-modality or multi-modality of the histogram as the statistics. If the histogram is multi-modal, it is preferable to calculate the statistics for each peak.

The statistics expressed by numeric values like this are called "summary statistics".

The statistics outputted by the statistics calculating unit 11 may be a value that indicates an average value, a median, a mode or the like of the oxygen saturation values in the region of interest. Thereby a representative value of the oxygen saturation can be known. If $x_i$ is the oxygen saturation value of the i-th pixel in the region of interest, and N is a number of pixels included in the region of interest, the average value of the oxygen saturation is given by Expression 6. The median is acquired as the N/2th oxygen saturation value when the oxygen saturation values of all the pixels in the region of interest are arranged in descending order or ascending order. The mode is the oxygen saturation value of which frequency is the highest when the histogram is generated.

[Math. 6]

$$\bar{x} = \frac{\sum_{i=1}^{N} x_i}{N}$$

(Expression 6)

The statistics outputted by the statistics calculating unit 11 may also be a variance, a standard deviation or a difference between a maximum value and a minimum value of the oxygen saturation values in the region of interest. By means of this, the dispersion of oxygen saturations in a region of interest may be obtained.

For example, if the oxygen saturations are dispersed in a region where the change of the oxygen saturation should be small, like the case of a region of interest that is small and in which it is expected that only one type of absorber exists, it is known that errors in measurement are large. In other words, the reliability of measurement can be known by determining the dispersion of oxygen saturations.

The standard deviation is calculated by Expression 7, and the variance is calculated by determining a square of the standard deviation. The difference between the maximum value and the minimum value is determined by calculating the difference between the maximum value and the minimum value of the oxygen saturation values of all the pixels in the region of interest.

[Math. 7]

$$s = \sqrt{\frac{\sum_{i=1}^{N} (\bar{x} - x_i)^2}{B}}$$

(Expression 7)

The statistics outputted by the statistics calculating unit 11 may also be a skewness or a kurtosis (a measure of sharpness) of the histogram. Thereby the success/failure of the measurement can be determined. Skewness $S_s$ can be calculated by Expression 8, and the kurtosis $S_k$ by Expression 9.

The statistics outputted by the statistics calculating unit 11 may also be a skewness or a kurtosis of the histogram. Thereby the success/failure of the measurement can be determined. Skewness $S_s$ can be calculated by Expression 8, and the kurtosis $S_k$ by Expression 9.

[Math. 8]

$$S_s = \frac{\sum_{i=1}^{N} (x_i - \bar{x})^3}{Ns^3}$$

(Expression 8)

[Math. 9]

$$S_k = \frac{\sum_{i=1}^{N} (x_i - \bar{x})^4}{Ns^4}$$

(Expression 9)

The statistics outputted by the statistics calculating unit 11 are not limited to the above mentioned examples, but can be any values that express the characteristics of the oxygen saturation. For example, [the statistics] may be a higher order statistics other than the above mentioned first order statistics. By calculating higher order statistics, characteristics as the image of the oxygen saturation distribution can be quantitatively known, and misrecognition due to optical illusion and perceptual illusion can be decreased. Examples of the higher order statistics are correlation, spatial frequency, spectral phase, gray level co-occurrence matrix and gray level difference matrix.

Statistics Display Examples

Examples of imaging various statistics calculated by the statistics calculating unit 11 will now be described with reference to FIG. 2A to FIG. 2D.

FIG. 2A to FIG. 2D are example of images that are generated by the image generating unit 13 and are outputted to the display device 14, and are examples of images of the calculated oxygen saturations expressed by brightness values and various statistics superposed on the image.

In the oxygen saturation distribution in the images shown in FIG. 2A to FIG. 2D, a signal portion (portion of upside down L shape) and the background portion (portion filled with black) are separated. This is implemented by the image generating unit 13 separating the signal portion and the background portion referring to the absorption coefficients, and generating an image that expresses only the oxygen saturation of the signal portion.

The signal portion is a portion that is regarded as an image of the absorber, and the background portion is a portion that is not regarded as an image of the absorber. These portions may be distinguished by setting a threshold in the absorption coefficient distribution, or by calculating signal probability based on the form of the signal of the absorption coefficient distribution or the initial sound pressure distribution, and setting a threshold.

For the absorption coefficient distribution or the initial sound pressure distribution that is used here, it is preferable to use the absorption coefficient distribution or the initial sound pressure distribution of a light source having a wavelength of which absorption coefficient of the oxyhemoglobin and the deoxyhemoglobin are similar. To calculate signal probability, a signal probability calculating unit may be disposed in the data processor 7 so that [the signal] is processed there. In this embodiment, an image is generated with separating the signal portion and the background portion, but this separation is not always necessary.

Figure 2A:
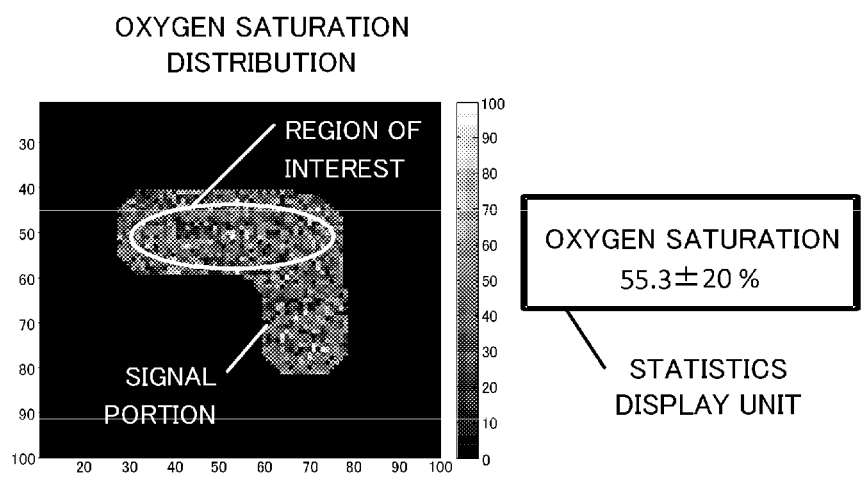
FIG. 2A to FIG. 2D show display examples of the photoacoustic diagnostic apparatus according to Embodiment 1.
Figure 2B:
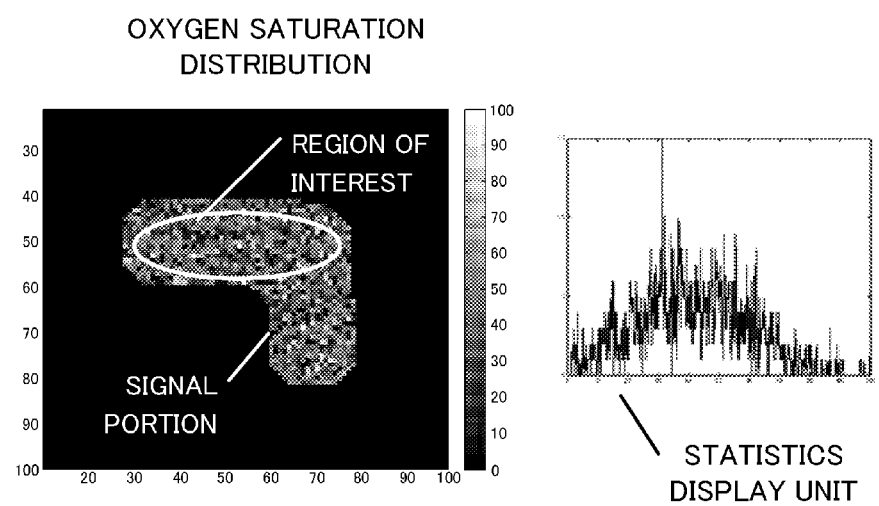
Figure 2C:
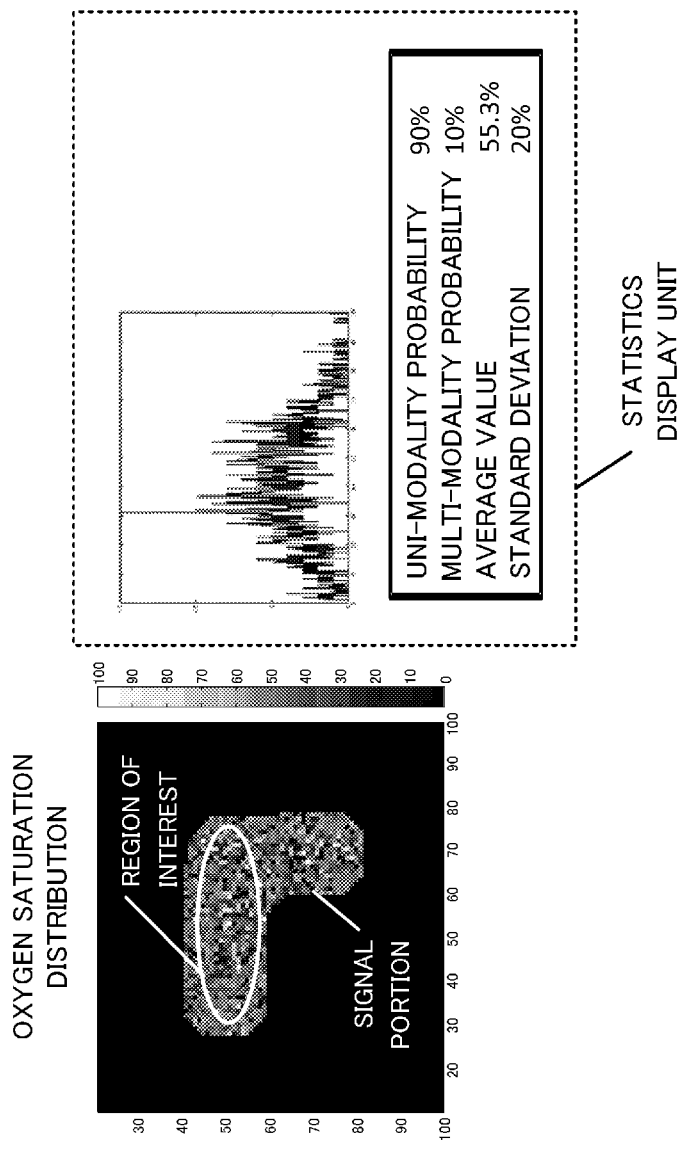
Figure 2D:
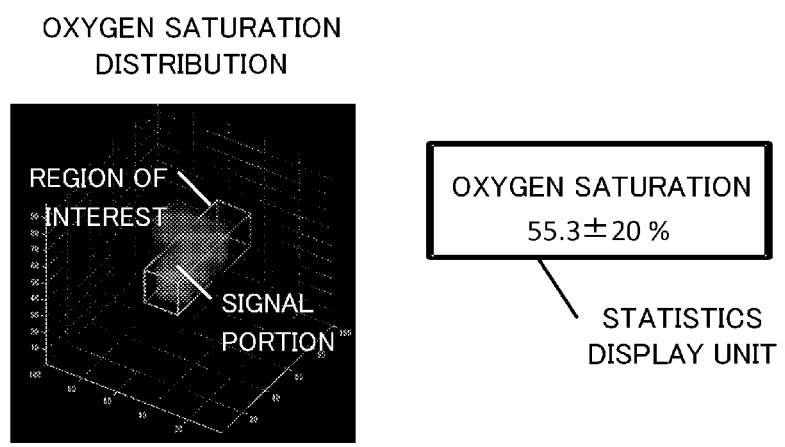

The ellipses indicated in FIG. 2A to FIG. 2C and the rectangular parallelepiped indicated in FIG. 2D are boundary lines of a region of interest that is set in the signal portion. The region of interest may be specified by drawing a boundary line or by changing a color tone inside the region of interest. If a plurality of regions of interest are set, the line to indicate each area and the color of the area may be changed depending on the area. Furthermore the operator may be able to switch the display/non-display of a region of interest.

FIG. 2A is an example when the average value and the standard deviation of the oxygen saturations are displayed as statistics. Here the average value and the standard deviation of the oxygen saturations in the region of interest are displayed as the representative value and an error of the oxygen saturations respectively. By this display, the operator can directly know the characteristics of the oxygen saturation distribution.

FIG. 2B is an example when a histogram is displayed as statistics. The histogram includes all the information on the first order statistics. Therefore the operator can examine various aspects by reading the characteristics of the oxygen saturation distribution via the histogram. If the histogram is multi-modal, summary statistics of each peak may be displayed. In this case, each peak may be detected automatically, or may be manually specified by the operator.

FIG. 2C is an example when not only the histogram but also the average value, the standard deviation, the probability that the distribution is uni-model, and the probability that the distribution is multi-modal are displayed. By this display, the histogram can be more easily examined. The reliability of the measurement may be calculated and displayed based on these statistics, or the success/failure of the measurement may be displayed based on a predetermined threshold of reliability.

FIG. 2D is an example when the oxygen saturation distribution of a three-dimensional region and a region of interest are displayed by volume rendering, and the summary statistics in the region of interest are displayed. It is more difficult to read a three-dimensional oxygen saturation distribution than a two-dimensional oxygen saturation distribution, but this display allows the operator to intuitively know the characteristics of the oxygen saturation.

The statistics display unit need not be disposed in a location adjacent to the oxygen saturation distribution, as shown in FIG. 2A to FIG. 2D. For example, [the statistics] may be semi-transparently displayed so as to be superposed on the image of the oxygen saturation distribution. To display both the histogram and the summary statistics, [the histogram and the summary statistics] may be displayed side by side or displayed in a superposed state. Further, the display/non-display of the statistics display unit may be switchable using such an interface as a mouse. Thereby the display space can be effectively used.

When a plurality of regions of interest are set, it is preferable to simultaneously display statistics in each region so that the statistics of each region can be compared. If the histogram is displayed, the comparison becomes easy by corresponding the color of the graph to the color of each region, and superposing [the graph and the region].

The images shown in FIG. 2A to FIG. 2D are examples. The image generating unit 13 can generate an image by combining arbitrary statistics if the statistics calculating unit 11 can calculate the statistics.

<Processing Flow Chart>

Figure 3:
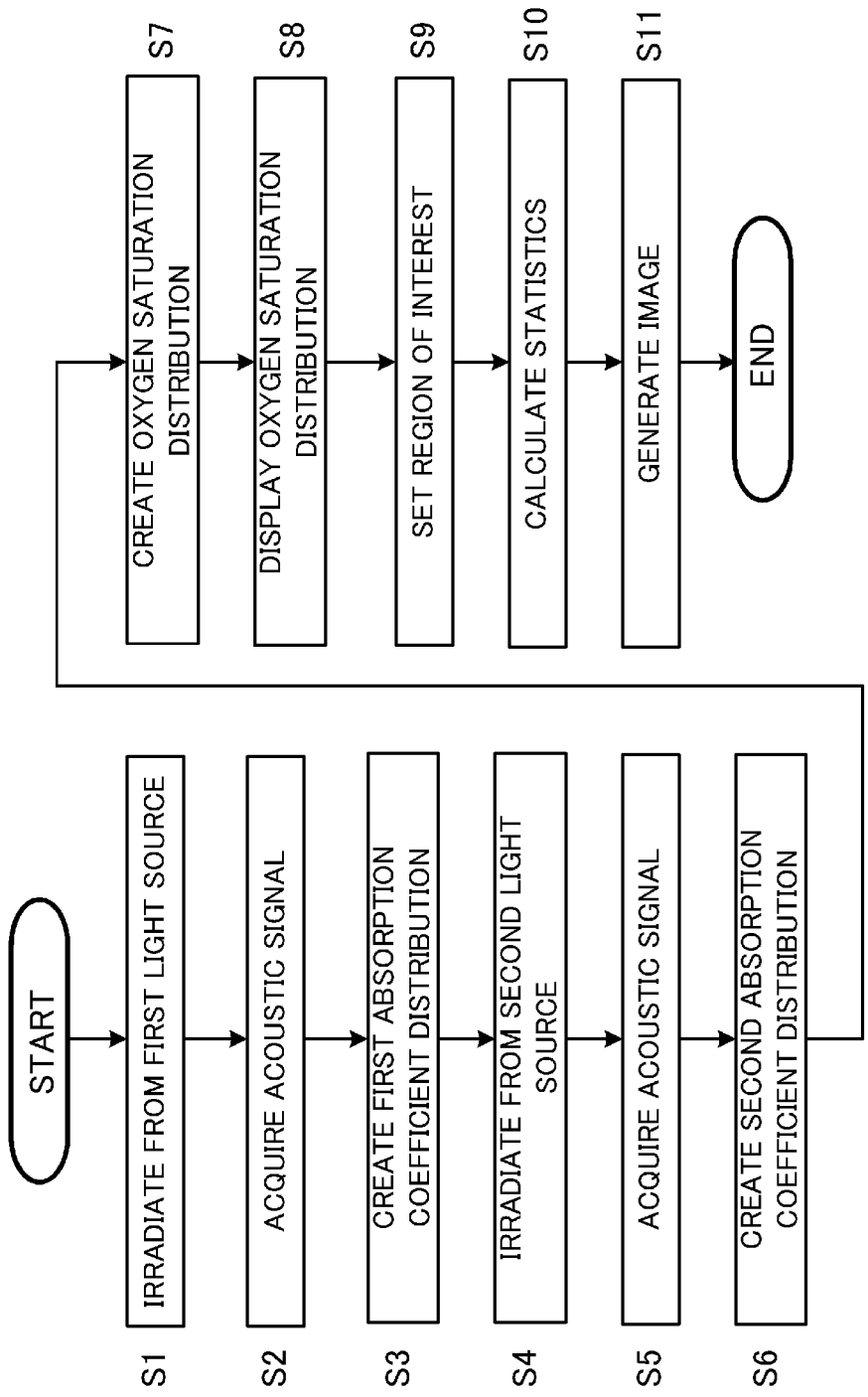
FIG. 3 is a flow chart depicting processing of the photoacoustic diagnostic apparatus according to Embodiment 1.

Processing performed by the photoacoustic apparatus according to Embodiment 1 will be described with reference to a processing flow chart in FIG. 3.

First in step S1, the first light source 1 irradiates an object with pulsed light.

In step S2, the acoustic detector 5 receives an acoustic wave generated from the object, and in step S3, the electric signal processor 6 converts the acoustic wave into a digital signal. Then the image reconstructing unit 8 generates an initial sound pressure distribution from this digital signal, and the light distribution correcting unit 9 generates a first absorption coefficient distribution. The generated first absorption coefficient distribution is transmitted to the comparison computing unit 10 and the image generating unit 13.

Step S4 to step S6 are steps of irradiating pulsed light onto the object using the second light source, and generating the second absorption coefficient distribution. Detailed description on these steps, which are the same as step S1 to S3, is omitted.

Then in step S7, the comparison computing unit 10 generates an oxygen saturation distribution using the acquired first and second absorption coefficient distributions. The generated oxygen saturation distribution is transmitted to the statistics calculating unit 11 and the image generating unit 13.

In step S8, the image generating unit 13 separates the signal portion and the background portion in the oxygen saturations received from the comparison computing unit 10, using the absorption coefficient distribution received from the light distribution correcting unit 9. Then [the image generating unit 13] generates an image on the oxygen saturation distribution of the signal portion only, and outputs the image to the display device 14. At this point, statistics are not superposed on the image displayed on the display device 14. After completing the processing in step S8, the operator can specify a region of interest.

In step S9, the region-of-interest setting apparatus 12 acquires information on the region of interest specified by the operator. The acquired information on the region of interest is transmitted to the statistics calculating unit 11.

In step S10, the statistics calculating unit 11 calculates the statistics inside the region of interest using the oxygen saturation distribution received from the comparison computing unit 10 and the information on the region of interest received from the region-of-interest setting apparatus 12. The calculated statistics are transmitted to the image generating unit 13.

In step S11, the image generating unit 13 updates the display image using the received statistics. In concrete terms, [the image generating unit 13] generates graphic information or text information that expresses the received statistics, and generates a new image by superposing this information on the image generated in step S8. The generated image is transmitted to the display device 14. Thereby both the oxygen saturation distribution and the statistics inside the region of interest are presented to the operator.

If the operator resets a region of interest, it is preferable that the regeneration of the statistics and the regeneration of the image (steps S10 and S11) are executed again. Thereby the change of the statistics can be observed in real-time, and the local characteristics of the oxygen saturation distribution can be easily known.

As described above, the photoacoustic diagnostic apparatus according to Embodiment 1 visualizes and presents the statistics inside the region of interest, along with the oxygen saturation distribution inside the object. Thereby the operator can know the characteristics of the oxygen saturation distribution, which observing the oxygen saturation distribution by images alone could not provide.

Embodiment 2

In Embodiment 2, not the oxygen saturation distribution but the absorption coefficient distribution is presented to the operator.

Figure 4:
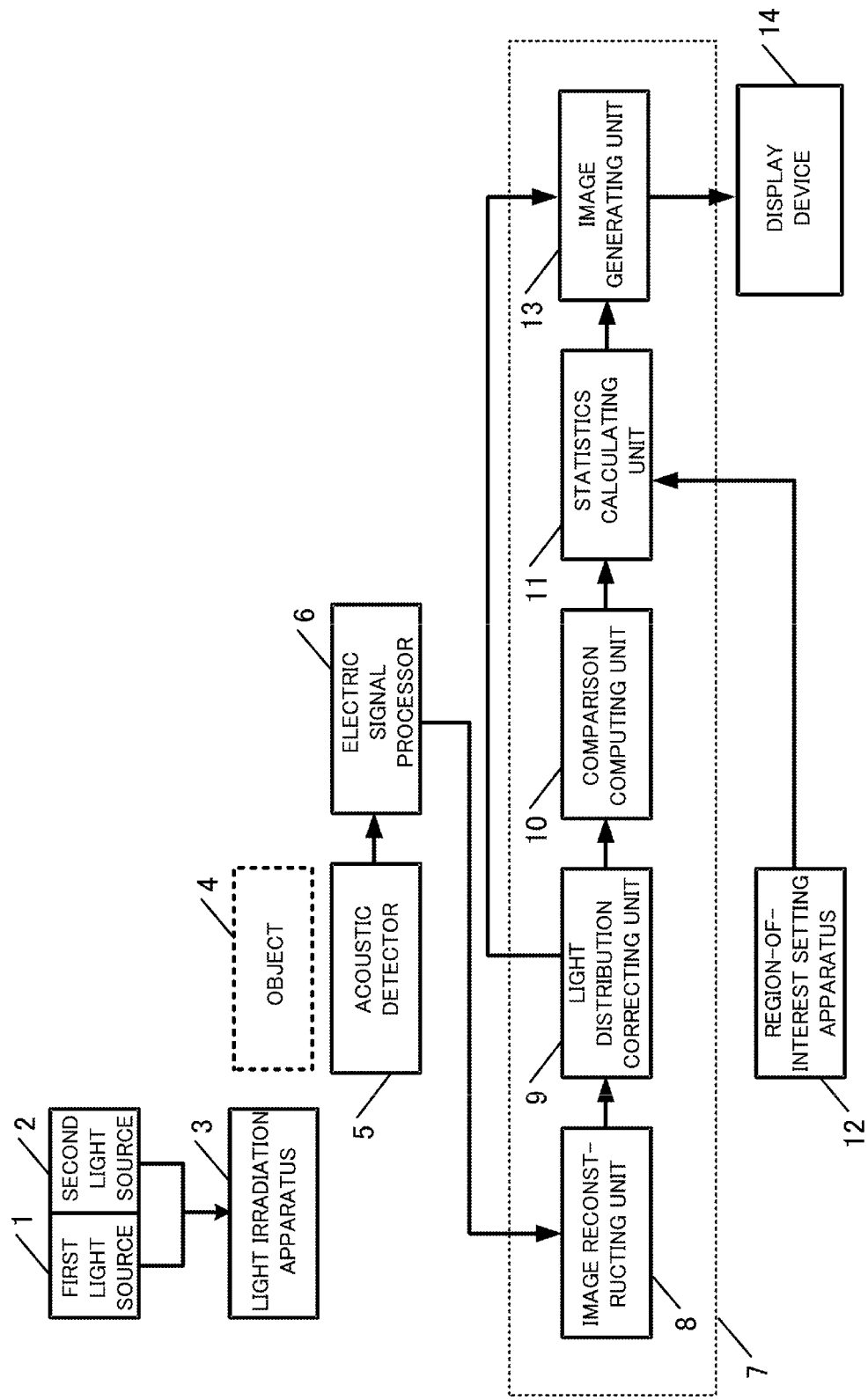
FIG. 4 is a diagram depicting a system configuration of a photoacoustic diagnostic apparatus according to Embodiment 2.

FIG. 4 shows a system configuration of a photoacoustic diagnostic apparatus according to Embodiment 2. The only difference of the system configuration of the photoacoustic diagnostic apparatus of Embodiment 2 from that of Embodiment 1 is that the oxygen saturation distribution is not transmitted from the comparison computing unit 10 to the image generating unit 13.

The only difference of the processing of the photoacoustic diagnostic apparatus of Embodiment 2 from that of Embodiment 1 is steps S7 and S8.

According to Embodiment 2, in step S7, the comparison computing unit 10 generates the oxygen saturation distribution using the acquired first and second absorption coefficient distributions. The generated oxygen saturation distribution is transmitted only to the statistics calculating unit 11.

In step S8, the image generating unit 13 generates an image expressing the absorption coefficient distribution using the absorption coefficient distribution received from the light distribution correcting unit 9. As a result, only the image expressing the absorption coefficient distribution is presented to the operator.

In other words, a region of interest, which the region-of-interest setting apparatus 12 acquires in step S9, is set based on the absorption coefficient distribution. Since the absorption coefficient distribution and the oxygen saturation distribution are on a same coordinate system, the region of interest that is set while checking the absorption coefficient distribution can be used as the region of interest in the oxygen saturation distribution.

In steps S10 and S11, the statistics calculating unit calculates the statistics of the oxygen saturation distribution in the region of interest, and the image generating unit 13 generates an image including the statistics, and outputs the image to the display device 14, just like Embodiment 1. The statistics that are used here can be arbitrary, as in the case of Embodiment 1.

Figure 5:
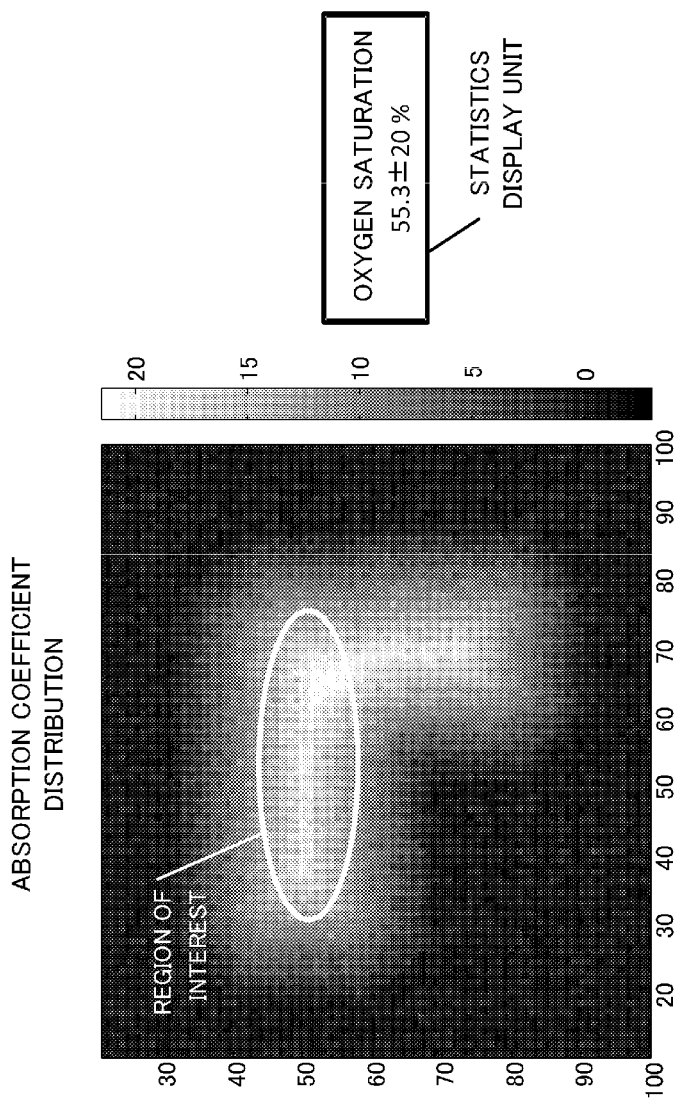
FIG. 5 shows a display example of the photoacoustic diagnostic apparatus according to Embodiment 2.

Thus according to Embodiment 2, the absorption coefficient distribution is presented to the operator and the operator sets a region of interest in the an object. A display image acquired as the result is as shown in FIG. 5. The absorption coefficient distribution and the region of interest that is set thereon are displayed, and summary statistics of the oxygen saturation, calculated based on the region of interest, is displayed. Statistics may include a histogram.

In this embodiment, only the absorption coefficient distribution is displayed, but one of the oxygen saturation distribution and the absorption coefficient distribution may be selectively displayed. The absorption coefficient distribution to be displayed may be a first absorption coefficient distribution or a second absorption coefficient distribution.

In Embodiment 1, if the absorption coefficient distribution includes many errors, and if the signal portion and the background portion cannot be separated in the oxygen saturation distribution, estimating a region where blood may exist on the image becomes difficult, and the region of interest cannot be set appropriately. In Embodiment 2, however, the absorption coefficient distribution can be displayed on screen, therefore even if the signal portion in the oxygen saturation distribution is obscured, the operator can determine the signal portion by checking the absorption coefficient distribution.

(Practical Examples)

The effect of the present invention was confirmed by an experiment. In this example, a hemispherical phantom is used as the object. The acoustic characteristic and the optical characteristic of the phantom base material are close to those of an organism, and an optical absorber is set inside the phantom in a position 25 mm from the surface of the object. The light absorption coefficient of the light absorber is approximately five times that of the phantom base material. The light absorber is uniform, and the average of the oxygen saturations is 80.3%.

The phantom is contacted by two holding plates, that are 10 mm thick and made from polymethylpentene, so as to sandwich phantom from both sides, and a 1 mm thick oil layer is disposed on the opposite side of one of the holding plates so that the acoustic detector is contacted via the oil layer.

Castor oil is used for the oil layer, and the element of the acoustic detector has a receiver of which diameter is 2 mm, and is constituted by PZT of which band is 80% at a 1 MHz center frequency. One acoustic detector is constituted by these elements, which are arranged 15×23 on a plane.

The acoustic detector is connected to an XY stage so that scanning is possible in the same plane direction as the plane of the acoustic detector.

A TiS laser is used for the first light source and the second light source, where the wavelength of the first light source is 756 nm, and the wavelength of the second light source is 797 nm. The pulsed lights in a nanosecond order generated by these light sources are simultaneously irradiated onto the object via the same plane as the acoustic detector and the opposite plane across from the object.

In the measurement, irradiation of the pulsed light, collection of acoustic wave signals, and scanning are repeated for each light source until all signal data is acquired. An A/D converter used for signal conversion has a 20 MHz sampling frequency and a 12-bit resolution.

Then the image reconstruction, the light distribution correction and the oxygen saturation calculation are performed using back projection, and initial sound pressure distribution, absorption coefficient distribution and oxygen saturation distribution, which are three-dimensional data, are acquired.

To separate the signal portion and the background portion, a second absorption coefficient distribution is used, and a region of interest is set by displaying the oxygen saturation distribution of the signal portion.

Figure 6:
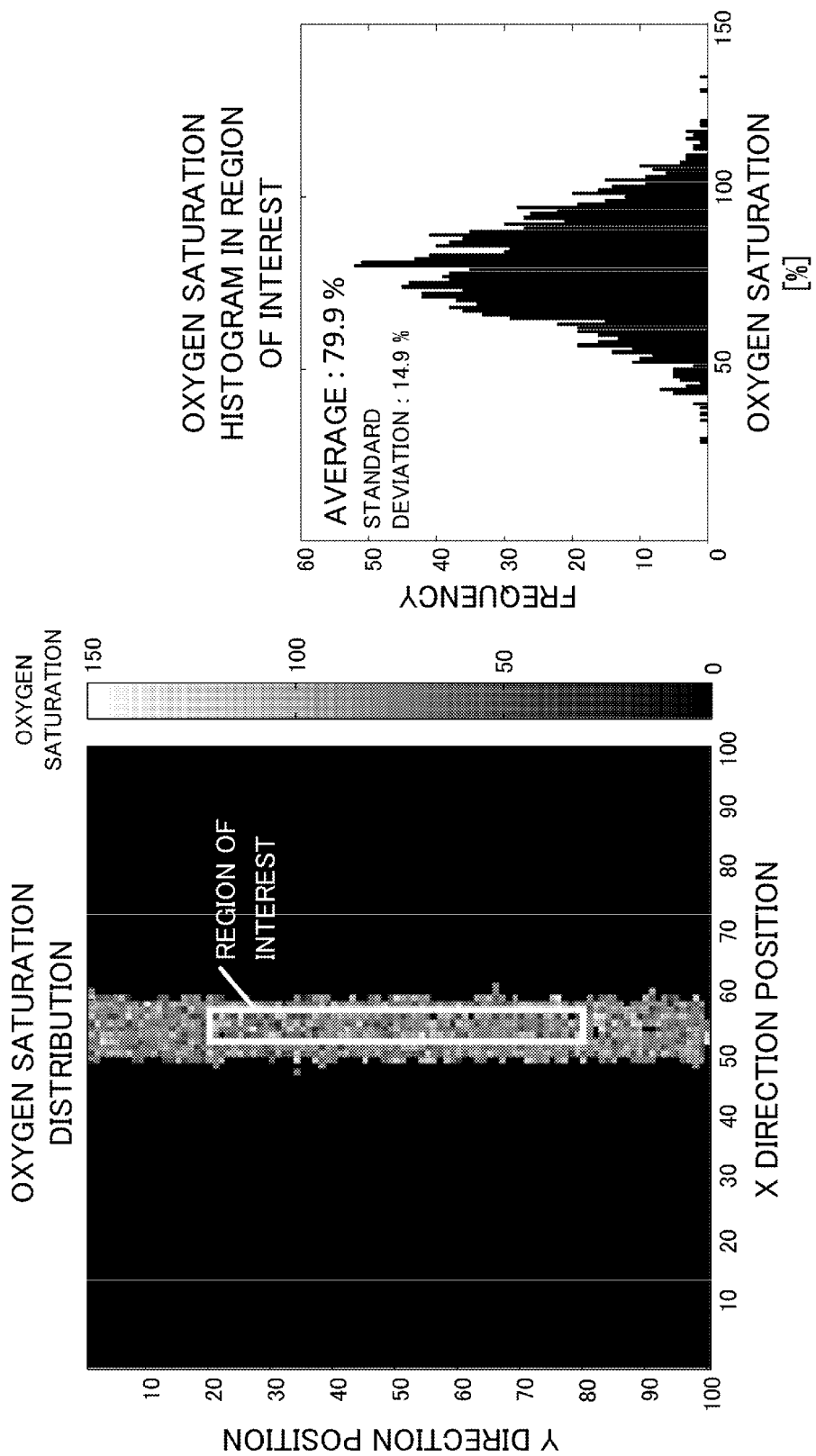
FIG. 6 is a display example according to a practical example.

FIG. 6 is the display screen acquired as the result. In FIG. 6, the region of interest is drawn on the oxygen saturation distribution, and the histogram, the average value and the standard deviation of the oxygen saturation in the region of interest are displayed on the right. By displaying the histogram, the oxygen saturation distribution in the region of interest can be checked in detail, and by displaying the average value and the standard deviation, diagnosis based on quantitative information can be performed.

(Modification)

Description on each embodiment is merely illustrative, and the present invention can be carried out by appropriately changing or combining within a scope not departing from the true spirit of the invention. The present invention may be carried out as a method of controlling an object information acquiring apparatus that includes at least a part of the above mentioned processing, or as a program to allow the object information acquiring apparatus to execute the method. The processing and the method can be freely combined as long as no technical inconsistency is generated.

For example, in the description of the embodiments, the region of interest is set and statistics corresponding to the area inside the region of interest are calculated and displayed, but the setting of the region of interest may be omitted, and the statistics on the entire region extracted as the signal portion may be generated.

In each embodiment, two light sources are used, but light sources having different wavelengths may be added so that three or more light sources are used.

A method of examining the content of a substance using a plurality of wavelengths, as illustrated in each embodiment, is called "spectroscopy". The measurement of the oxygen saturation is one spectroscopic technique. In the description of the embodiments, a method of calculating the oxygen saturation was described, but the detection target may be a different substance. For example, the content rate of water, melanin, collagen, lipids or the like can be calculated in the same manner using a wavelength of which absorbent to the substance is high.

The problem the present invention is to solve is not limited to the oxygen saturation, and since the same calculation method is used, [the solution] is common to the technique of calculating the content rate using spectroscopy. Therefore the scope of the present invention is not limited to the oxygen saturation, but can include the content rate of other substances determined by using spectroscopy. In the description of the present invention, the oxygen saturation may be read as a content rate of another substance.

OTHER EMBODIMENTS

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-286549, filed on Dec. 28, 2012, which is hereby incorporated by reference herein in its entirety.

What is claimed is:

1. An object information acquiring apparatus comprising:
a light irradiation unit configured to irradiate an object with first light having a first wavelength and second light having a second wavelength different from the first wavelength;
an acoustic wave receiving unit configured to receive an acoustic wave that is generated from the object by irradiation of the object with the first light and by irradiation of the object with the second light, and convert the received acoustic wave into a first electric signal that corresponds to the first light and a second electric signal that corresponds to the second light;
an oxygen saturation acquiring unit configured to acquire first image data on an oxygen saturation distribution indicating oxygen saturation in the object based on the first electric signal and the second electric signal;
an image data acquiring unit configured to acquire second image data on an absorption coefficient distribution in the object, based on the first electric signal or the second electric signal;
a region of interest setting unit configured to set at least one region of interest based on a designation by a user for the second image data and apply the at least one region of interest to the first image data;
a statistics information acquiring unit configured to:
(a) calculate a histogram of the first image data included in the at least one region of interest;
(b) calculate a value indicating uni-modality or multi-modality in the histogram by differentiating the histogram and counting a number of locations where the sign of a differentiated value of the histogram is inverted; and
(c) calculate a reliability of a measurement based on the value indicating the uni-modality or multi-modality in the histogram; and
an image generating unit configured to (a) generate an image including (i) the second image data, (ii) the at least one region of interest on the second image data, and (iii) the reliability of the measurement, and (b) cause a display device to display the image.

2. The object information acquiring apparatus according to claim 1, wherein the image generating unit is configured to generate the image including the histogram of the first image data.

3. The object information acquiring apparatus according to claim 1, wherein the region of interest setting unit is configured to set at least one reset region of interest, different from the at least one region of interest, based on a designation by the user for on the second image data, wherein the statistics information acquiring unit is configured to:

calculate a reacquired histogram of the first image data included in the at least one reset region of interest;

calculate a reacquired value indicating uni-modality or multi-modality in the reacquired histogram by differentiating the reacquired histogram and counting a number of locations where the sign of a differentiated value of the reacquired histogram is inverted, and calculate a reacquired reliability of the measurement based on the reacquired value indicating the uni-modality or multi-modality in the reacquired histogram, and wherein the image generating unit is configured to generate reacquired image including the second image data, the at least one reset region of interest on the second image data, and the reacquired reliability of the measurement, and to cause the display device to display the reacquired image.

4. The object information acquiring apparatus according to claim 1, wherein the region of interest setting unit is configured to set a first region of interest and a second region of interest different from each other based on the second image data, as the at least one region of interest, wherein the statistics information acquiring unit is configured to acquire a first reliability of the measurement corresponding to the first region of interest and a second reliability of the measurement corresponding to the second region of interest, and wherein the image generating unit is configured to generate the image including the first reliability of the measurement corresponding to the first region of interest, and the second reliability of the measurement corresponding to the second region of interest.

5. The object information acquiring apparatus according to claim 4, wherein the region of interest setting unit is configured to:

set a whole region of the second image data, as the first region of interest, and set a part region of the second image data, as the second region of interest.

6. The object information acquiring apparatus according to claim 1, wherein the statistics information acquiring unit is configured to calculate skewness or sharpness of the histogram, and wherein the image generating unit is configured to generate the image including the skewness or sharpness of the histogram.

7. The object information acquiring apparatus according to claim 1, wherein the oxygen saturation acquiring unit is configured to acquire the first image data in three-dimensional space, wherein the image data acquiring unit is configured to acquire the second image data in three-dimensional space, and wherein the region of interest setting unit is configured to set the at least one region of interest in three-dimensional space based on a designation by the user for the second image data.

8. The object information acquiring apparatus according to claim 1, wherein the statistics information acquiring unit is configured to calculate an average value, a median value, or a mode of the first image data included in the at least one region of interest, and wherein the image generating unit is configured to generate the image including the average value, the median value, or the mode of the first image data included in the at least one region of interest.

9. The object information acquiring apparatus according to claim 1, wherein the statistics information acquiring unit is configured to calculate a variance, a standard deviation, or a difference between a maximum value and a minimum value of the first image data included in the at least one region of interest, and wherein the image generating unit is configured to generate the image including the variance, the standard deviation, or the difference between the maximum value and the minimum value of the first image data included in the at least one region of interest.

10. The object information acquiring apparatus according to claim 1, wherein the region of interest setting unit is configured to set a part region of the second image data, as the at least one region of interest.

11. The object information acquiring apparatus according to claim 1, wherein the statistics information acquiring unit is configured to calculate a representative value and a dispersion of the first image data included in the at least one region of interest, and wherein the image generating unit is configured to generate the image including text representing the representative value and the dispersion of the first image data included in the at least one region of interest.

12. The object information acquiring apparatus according to claim 1, wherein the second image data is obtained by a calculation including dividing a sound pressure distribution by a light distribution.

13. An object information acquiring apparatus comprising:

an oxygen saturation acquiring unit configured to acquire first image data on an oxygen saturation distribution indicating oxygen saturation in an object;

an image data acquiring unit configured to acquire second image data on an absorption coefficient distribution in the object;

a region of interest setting unit configured to set at least one region of interest based on a designation by a user for the second image data and apply the at least one region of interest to the first image data;

a statistics information acquiring unit configured to:

(a) calculate a histogram of the first image data included in the at least one region of interest;

(b) calculate a value indicating uni-modality or multi-modality in the histogram by differentiating the histogram and counting a number of locations where the sign of a differentiated value of the histogram is inverted; and (c) calculate a reliability of a measurement based on the value indicating the uni-modality or multi-modality in the histogram, and an image generating unit configured to (a) generate image including (i) the second image data, (ii) the at least one region of interest on the second image data, and (iii) the reliability of the measurement, and
(b) cause a display device to display the image.

14. A display method comprising:
displaying a first image on an absorption coefficient distribution in an object which is generated based on a received signal of an acoustic wave that is generated from the object by irradiation of the object with light;
setting at least one region of interest based on a designation by a user for the displayed first image;
calculating a histogram of the first image data included in the region of interest;
calculating a value indicating uni-modality or multi-modality in the histogram by differentiating the histogram and counting a number of locations where the sign of a differentiated value of the histogram is inverted;
calculating a reliability of a measurement based on the value indicating the uni-modality or multi-modality in the histogram;
generating a second image including (i) the first image, (ii) the at least one region of interest on the first image, and (iii) the reliability of the measurement; and
displaying the second image.

15. A non-transitory computer program readable storage medium recording a computer program for causing a computer to perform a method comprising the steps of the display method according to claim 14.

* * * * *